United States Patent [19]

Parish et al.

[11] Patent Number: 4,885,311
[45] Date of Patent: Dec. 5, 1989

[54] TOPICAL TRANSRETINOIDS FOR TREATMENT OF ACNE AND SKIN DISEASES

[75] Inventors: Harlie A. Parish; William P. Purcell, both of Memphis, Tenn.

[73] Assignee: Molecular Design International, Memphis, Tenn.

[21] Appl. No.: 67,536

[22] Filed: Jun. 29, 1987

[51] Int. Cl.$^4$ .................. A61K 31/23; C11C 3/02; C07D 213/46; C07D 307/02

[52] U.S. Cl. .................. 514/549; 260/404; 260/405.5; 260/410.5; 260/410.9 V; 514/350; 514/423; 514/425; 514/461; 514/547; 546/314; 548/530; 549/255; 549/488; 549/70

[58] Field of Search .................. 514/423, 425, 350, 461, 514/547, 549; 546/314; 548/530; 549/255, 488; 260/410.9 V, 404, 405.5, 410.5

[56] References Cited

U.S. PATENT DOCUMENTS

| | | | |
|---|---|---|---|
| 2,424,994 | 8/1947 | Milas | 260/410.9 V |
| 2,576,103 | 11/1951 | Cawley et al. | 260/410.9 V X |
| 2,917,523 | 12/1959 | Pommer et al. | 260/410.9 V |
| 2,951,853 | 9/1960 | Matsui | 260/410.9 V X |
| 3,984,544 | 10/1976 | Casmer et al. | 514/177 |
| 4,055,659 | 10/1977 | Gander et al. | 514/552 |
| 4,108,880 | 8/1978 | Gander et al. | 260/410 |
| 4,190,594 | 2/1980 | Gander et al. | 260/404 |
| 4,216,224 | 8/1980 | Yu et al. | 514/561 |
| 4,529,600 | 7/1985 | Dawson et al. | 514/529 |
| 4,677,120 | 6/1987 | Parish et al. | 514/549 |

FOREIGN PATENT DOCUMENTS

| | | |
|---|---|---|
| 0106926 | 5/1984 | European Pat. Off. . |
| 2050658 | 5/1972 | Fed. Rep. of Germany . |
| 2081478 | 12/1971 | France . |

Primary Examiner—Werren B. Lone
Assistant Examiner—Vera C. Clarke
Attorney, Agent, or Firm—Waldron & Associates

[57] ABSTRACT

Esters and amides of 13-trans-retinoic acid are disclosed which are used for the treatment of acne and skin diseases.

14 Claims, No Drawings

TOPICAL TRANSRETINOIDS FOR TREATMENT OF ACNE AND SKIN DISEASES

BACKGROUND OF THE INVENTION

1. Field of the Invention

Retinol (vitamin A) and retinoic acid (vitamin A acid), its isomers, and certain of its analogs are known to have beneficial effects in the treatment of acne and keratinizing skin disorders.

Acne affects large patient populations and is a common inflammatory skin disorder which usually localizes on the face. Fortunately, the disease usually disappears and in the interval of months or years between onset and resolution, therapy, although not curative, can satisfactorily suppress the disease in the majority of patients.

A small number of acne patients with severe disease show little or no response to intensive therapeutic efforts including the use of high doses of oral tetracycline, dapsone, prednisone, and, in women, estrogen. In many cases, these drugs afford only a modest degree of control while the side effects of these agents severely restrict their usefulness. Patients with nodulocystic acne suffer from large, inflammatory, suppurative nodules appearing on the face, and frequently the back and chest. In addition to their appearance, the lesions are tender and often purulently exudative and hemorrhagic. Disfiguring scars are frequently inevitable.

Therapies for acne involve local and systemic administration of vitamin compounds, collectively know as retinoids. Topical application of all-trans-retinoic acid has been tried with some success, particularly against comedones or blackheads, but this condition frequently returns when the treatment is withdrawn. (All-trans-retinoic acid is also known as tretinoin. These terms are used interchangeably throughout this specification.) Additionally, retinoic acid applied topically can be highly irritating and its use can be painful for the patient depending on the concentration used and the frequency of application.

A number of side effects complicates the administration of large doses of vitamin A. Among the many symptoms of hypervitaminosis A are weight loss, desquamation of the skin, hair loss, irritation of the oral and pharyngeal mucosa, and nose bleeds, headaches, bone pain, liver toxicity due to storage of vitamin A in the liver, papilledema, pseudotumor cerebri, demineralization, and periosteal thickening of the bones. Because of these and other side effects of oral treatment with vitamin A and all-trans-retinoic acid, which produces similar side effects, they are rarely recommended for dermatopathic conditions.

The present invention relates to 13-trans-retinoic acid esters which are effective in the treatment of acne and other skin disorders when administered either topically or orally and which show few if any side effects.

2. Description of the Prior Art

The "Handbook of Nonprescription Drugs," 5th ed., 1977, A.P.A. pub., pp. 140, 319, 320, discloses the use of vitamin A and retinoic acid in the treatment of acne (unspecified). However, the disclosure of this publication is opposite to that of the subject invention, in that it states, "The systemic use of vitamin A for the treatment of acne, . . . is not warranted by clinical evidence" at p. 140; and that, "Treatments that have been abandoned or have not been proved effective include oral vitamin A" at p. 320.

J.V. Straumford reported a systemic usage of large oral doses of retinol, the alcohol form of vitamin A, over a long period of time for the treatment of acne. (Straumford, J. V., "Vitamin A: Its Effect on Acne," Northwest Med., 42: 219-255, August, 1943.) These results, however, have been disputed and systemic therapy of acne utilizing retinol has been challenged by other investigators. (Anderson, J. A. D., et al., "Vitamin A in Acne Vulgaris," Brit. Med. J., 2: 294-296, August, 1963; Lynch, F. W., et al., "Acne Vulgaris Treated with Vitamin A," Arch. Derm. 55: 355, 357, March, 1947; and Mitchell, G. H., et al., "Results of Treatment of Acne Vulgaris by Intramuscular Injections of Vitamin A,"Arch. Derm. 64: 428-434. October, 1951.)

Topical administration of retinoic acid for the treatment of acne was reported by Kligman, et al., (Arch. Derm. 99: 469-476, 1969, U.S. Pat. No. 3,729,568). The effectivenesss of this treatment as disclosed by Kligman is often associated with a noticeable irritating effect of topically applied retinoic acid.

Esters and amides of trans-retinoic acid which are useful for the treatment of acne are claimed in U.S. Pat. Nos. 4,055,659 (all-trans-retinoyloxyacetamide), 4,126,697 (4-(all-trans-retinoyloxyacetyl)-catechol), 4,126,698 (2-hydroxyethyl all-trans-retinoate), and 4,304,787 (benzyl all-trans-retinoate). All four of these patents to Gander, et al. also disclose mixed 2-hydroxy-1-propyl and 1-hydroxy-2-propyl all-trans-retinoates, N-(3,4-methylenedioxyphenylmethyl) all-trans-retinamide, and 4-nitrobenzyl all-trans-retinoate. The effectiveness of all these compounds was shown through testing which measured increase in DNA synthesis in epidermal cells. This ability has been associated with the effectiveness of retinoic acid in the treatment of acne. See, for example, Christophers and Braun-Falco, "Stimulation of Epidermal DNA-Synthesis with Vitamin A-Acid," Arch. Klin. Exp. Derm. 232: 427-433 (1968) and Wolfe, et al., "Changes in Epidermal Differentiation After Vitamin A Acid," Arch. Klin. Exp. Derm. 237: 744-795 (1970). No claim is made and no testing is disclosed in the Gander, et al. patents which indicates that the esters or amides show fewer or greater side effects than trans-retinoic acid.

The process for treating acne vulgaris topically utilizing retinal, the aldehyde form of vitamin A, is disclosed in U.S. Pat. No. 3,932,665. The aldehyde form, unlike the acid form of vitamin A, exerts its therapeutic effect without producing irritation, inflammation, erythema, or peeling of the skin. This patent also discloses the topical use of 13-cis-retinal in the treatment of acne vulgaris.

The method of treating acne with C-20 and C-22 vinylogs of desmethyl retinoic acid is disclosed in U.S. Pat. No. 3,882,244. These vinylogs as disclosed in the patent are applied topically to the site of the acne infection as a solution, ointment, or powder. The treatment of acne vulgaris with retinoic acid analogs particularly 11-(2',6',6'-trimethylcyclohex-1'-enyl-1')-5,9-dimethylundeca-2,4,6,8,10-pentenoic acid is disclosed in U.S. Pat. No. 3,934,028. This compound can be used either internally or topically. When taken orally, the daily dosage of this compound ranged from 30-300 mg taken over from 2 to 8 weeks. However, there is no indication that the compound leads to remission from the disease after administration of the compound is withdrawn.

Other drugs presently used in the treatment of acne include benzoyl peroxide, tretinoin (all-trans-retinoic acid, Retin-A-Ortho), clindamycin, tetracyline, erythromycin, minocycline, and estrogens (for females).

Benzoyl peroxide is considered safe and effective in mild and moderate acne treatment. Tretinoin is effective but has the previously mentioned deleterious side effects, as well as accelerating photocarcinogenesis. The antiboitics are reasonably effective but have side effects such as gastrointestinal problems including reports of pseudomembranous colitis. Estrogens are sometimes effective in treating acne, but the side effects of these drugs make them less than desirable.

The use of 13-cis-retinoic acid derivatives for the treatment of acne and other skin diseases is disclosed in U.S. Pat. No. 4,677,120 of Parish et al. The derivatives are claimed for use in either oral or topical treatment of the disease. These derivatives have been found to minimize the toxic side-effects associated with the use of 13-cis-retinoic acid in the treatment of acne.

A prodrug that would retain the effectiveness of retinoic acid and would be essentially free of the deleterious side effects of retinoic acid would provide a much needed solution to a widespread problem.

SUMMARY OF THE INVENTION

This invention is directed to novel derivatives of trans-retinoic acid which are useful in the treatment of acne but which minimize the toxic side-effects associated with trans-retinoic acid treatments of acne.

The derivatives have the formula:

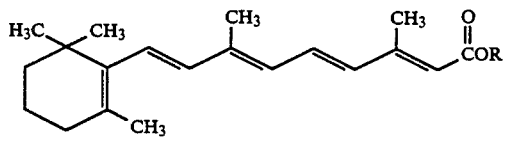

wherein R is

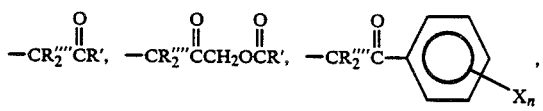

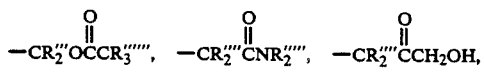

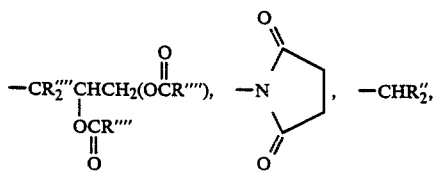

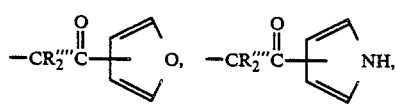

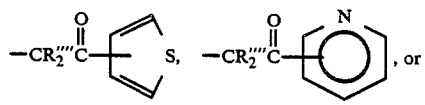

-continued

wherein X is —H, —F, —Cl, —Br, —I, —OH, —OR, —OR',

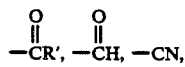

—CN, —NO$_2$, —NH$_2$, —NHR', or —NR'$_2$;
wherein n is a number from 1 to 5;
wherein R' is H or any of the lower alkyls ranging from C$_1$ to C$_6$;
wherein R" is

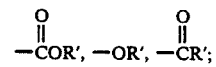

or R';
wherein R''' is the hydrocarbon backbone of fatty acids;
wherein R'''' is R' or the hydrocarbon backbone of fatty acids;
wherein R''''' is the lower alkyls ranging from C$_1$ to C$_6$;
and further,
where the are two or more R', R", R''', R'''', or R''''' groups attached to the same carbon, each R', R", R''', R'''', or R''''' group may be the same as or different from the other R', R", R''', R'''', or R''''' groups attached to that carbon.

These derivatives can be applied topically or orally without causing irritation or with less irritation than found with state of the art treatments, and are an effective and safe treatment for acne.

While it is believed that these compounds are useful for the treatment of acne, it is also suggested that they are useful for treatment or amelioration of the same additional classes of skin disorders as is retinoic acid itself. These disorders include ichthyoses (e.g., ichthyosis hystrix, epidermolytic hyperkeratosis, and lamellar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dematoses (e.g., elastosis perforans seripiginosa and Kyrle's disease), and disorders of keratinization (e.g., Darier's disease, keratoderma, hyperkeratosis plantaris, pityriasis rubra pilaris, lichen planus acanthosis nigricans, and psoriosis).

TOPICAL ASSAY

A topical assay to test for pseudocomedone (utriculus) reduction in the rhino mouse was conducted.

Each test compound and a vehicle control was applied topically to the dorsal trunk of the rhino mouse. The utriculus diameters were measured with a ocular micrometer. The assay is unique and proprietary to Ortho Pharmaceutical Corp. and is based upon the work of Kligman, et al. (1979) and Van Scott (1972). Kligman, et al., "The Effect on Rhino Mouse Skin of Agents which Influence Keratinization and Exfoliation," J. Invest. Derm. 73: 354–358 (1979). Van Scott, "Experimental Animal Integumental Models for Screening Potential Dermatologic Drugs," In *Pharmacology of the Skin*, eds. Montagna et al., New York, Appleton-Century-Crofts, 1972, pp. 523–533. Mann, "Hair Loss and Cyst Formation in Hairless and Rhino Mutant Mice," Anat. Rec. 170: 485–500 (1971). Mezick, et al., "Topical and Systemic Effects of Retinoids on Horn-Filled Utriculus Size in the Rhino Mouse. A Model to Quantify Antikeratinizing Effects of Retinoids," J. Invest. Derm. 83: 110–113 (1984). Mezick, et al., "Anti-Acne Activity of Retinoids in the Rhino Mouse," In *Models in Dermatology*, eds. Maibach, et al., Basel, Karger, 1985.

The dorsal trunk of the rhino mouse was the test site. Each test compound was dissolved in alcohol:propylene glycol (70:30, v:v) or other suitable vehicle and topically applied (0.1 ml) to the dorsal trunk once daily, five consecutive days/week for two weeks. Also, administration could be oral (p.o.) in a suitable vehicle. Following treatment, the animals were sacrificed by cervical dislocation. The treated dorsal trunk skin was removed from the animal and placed into 0.5% acetic acid for up to 18 hours at approximately 4° C. After this, the epidermis with the "acne cysts" was separated from the underlying dermis. The sheets of epidermis were processed by routine methods to permanent whole mounts for microscopic examination. Also, full-thickness samples could be taken, stained (H&E), and examined by light microscopy.

The utriculus diameters were measured with an ocular micrometer to compare effects of test compounds to vehicle control and/or reference compound on cyst reduction. Light microscopy was used to determine effects on cell differentiation. The results are summarized in Table 1:

TABLE 1

TOPICAL RHINO MOUSE ASSAY

| RETINOID | % CONCENTRATION | % UTRICULUS REDUCTION |
|---|---|---|
| Cpd. 1 | 0.1 | 61.6 |
| Cpd. 2 | 0.1 | 46.9 |
| all-trans-retinoic acid | 0.1 | 69.0 |

All-trans-retinoic acid was used as a control. Cpd. 1 and Cpd. 2 have the formulas identified in the examples below.

From the results it can be seen that the compounds of the invention were effective in topical applications. The data presented is raw data which does not take into account the differences in molecular weight between the compounds of the invention and all-trans-retinoic acid. A further advantage of the compounds is their non-irritating characteristic when applied topically. This highly desirable characteristic is not seen when all-trans-retinoic acid is used.

The compounds of the invention may be topically applied to the acne site in any suitable pharmaceutically-acceptable vehicle, as for example, a liquid carrier such as propylene glycol-ethanol, propylene glycol-ethanol-chloroform, and the like. A preferred liquid composition is a solution of a small amount of at least one of the compounds of the invention in a combination of (A) from about 25% to about 75% by volume of 95% ethanol and (B) from about 75% to about 25% by volume of a liquid glycol. A typical solvent carrier of this type comprises 70% by volume 95% ethyl alcohol and 30% by volume propylene glycol. The preferred concentration of the active compound in these compositions is at least about 0.01% by weight, more preferably from about 0.01% to about 0.5% by weight, and most preferably from about 0.05% to about 0.2% by weight, but any therapeutically effective concentration may be used. This method of use is similar to the method taught in U.S. Pat. # of Harlie, et al. These compositions and the method of treating acne by topical application to the acne site of at least one of the compounds of the invention are considered part of the present invention. Although topical application of the compounds of the invention is the preferred method of application, oral dosages of the compounds of the present invention are potentially effective.

The preparation of the compounds of the present invention is illustrated by the following examples. For each of the examples, melting points in each of the examples were determined on a Thomas-Hooever capillary point apparatus, 1H-NMR spectra were taken with a Varian EM-360-A spectrometer, and elemental analysis was done by Atlantic Microlab, Inc., of Atlanta, Ga.

EXAMPLE 1 synthesis of compound 1

1-(all-trans-retinoyloxy)-2-propanone

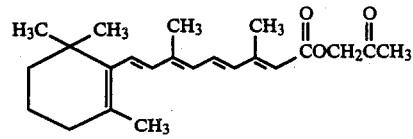

Into a 100 ml round bottom flask was added 1.0 g (0.0033 moles) of tretinoin (retinoic acid from Sigma Chemical Co., St. Louis, MO), 25 ml of anhydrous methanol, and 0.2 g (0.0035 moles) of KOH. The solution was stirred at room temperature until the tretinoin dissolved. After the solvent was removed under vacuum, 25 ml of acetonitrile was added and the solution was again concentrated to a semisolid under vacuum. Chloroacetone, (2.0 g, 0.032 moles), 0.1 g 18-crown-6 (0.00038 mole), and 100 ml of acetonitrile were added. The solution was stirred for 24 hours at room temperature with a magnetic stirrer. The sample was concentrated to about 5 ml and chromatographed on a neutral aluminum oxide (Aldrich #19, 997-4) column (14×1.8 cm). The alumina was deactivated with 20 ml of water per 1.0 kg of alumina.

The sample was eluted stepwise with 100 ml of 20% dichloromethane in hexane, 100 ml of 50% dichloromethane in hexane, and finally with 250 ml of dichloromethane. The sample eluted quickly and the vast majority of the impurities remained on the column. Fractions of 25 ml were collected and evaluated by thin layer chromatography (TLC) on silica gel (EM Reagents #5775) developed with ethyl acetate:heptane (1:3). The fractions containing the product were combined and concentrated to give an orange oil which solidified on cooling to give 0.55 g of solid.

Triturating the sample with 10 ml of cold 95% ethanol raised the melting point to 93°–94° C.

TLC on silica gel (EM Reagents #5735) developed with 1:3 ethyl acetate:heptane showed one spot, $R_f=0.41$. TLC on aluminum oxide (EM Reagents

5581) developed with 1:3 ethyl acetate:heptane showed one spot, $R_f=0.73$.

The NMR (CDCl$_3$) spectrum of Compound 1 was identical to the spectrum of tretinoin except for two additional peaks and the lack of a carboxylic acid peak. The two additional peaks were at 4.5 ppm (singlet, 2 protons, —OCH$_2$CO—) and 2.1 ppm (singlet, 3 protons —COCH$_3$).

Elemental analysis for the compound gives a theoretical value for C$_{23}$H$_{32}$O$_3$ of 77.49% C, 9.05% H; the found values were 77.52% C and 9.17% H.

EXAMPLE 2 synthesis of compound 2

2-(all-trans-retinoyloxy)-4'-methoxyacetophenone

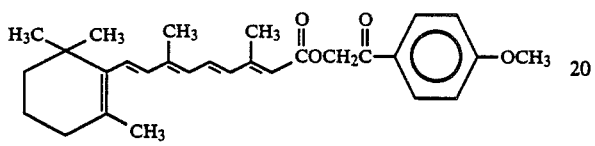

The procedure used in Example 1 was followed with minor modifications. The reaction was carried out in a 250 ml round bottomed flask with 1.0 g of tretinoin and a 20% molar excess of 2-chloro-4'-methoxyacetophenone. (2-chloro-4'-methoxyacetophenone was prepared from the Friedel-Crafts acylation of anisole with chloroacetic anhydride.) After completion of the reaction, the product was isolated by column chromatography under the same conditions as in Example 1 except that a larger column (11 cm×4 cm diameter) was used. The product (1.9 g, m.p. 118°–124° C.) at this point, however, contained unreacted 2-chloro-4'-methoxyacetophenone. A homogeneous product was obtained by recrystallization form 100 ml of 95% ethanol to give 0.88 g, melting point 125°–126° C., of a yellow solid.

TLC on silica gel (EM Reagents #5735) developed with 1:3 ethyl acetate:heptane showed one spot, $R_f=0.45$. TLC on aluminum oxide (EM Reagents #5581) developed with 1:3 ethyl acetate:heptane showed one spot, $R_f=0.69$.

The NMR (CDCl$_3$) spectrum of Compound 2 was identical to the spectrum of tretinoin except for three additional peaks and the lack of a carboxylic acid peak. The three additional peaks were at 3.8 ppm (singlet, 3 protons —OCH$_3$), 5.2 ppm (singlet, 2 protons, —OCH$_2$CO—), and 6.60, 6.75, 7.55, and 7.70 ppm (quadruptlet, 4 protons, aromatic ring).

Elemental analysis for the compound gives a theoretical value for C$_{29}$H$_{36}$O$_4$ of 77.64% C, 8.09% H; the found values were 77.58% C and 8.10% H.

What is claimed is:

1. A compound of the formula:

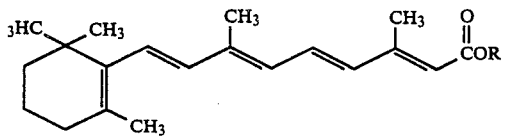

wherein R is a member of the group consisting of:

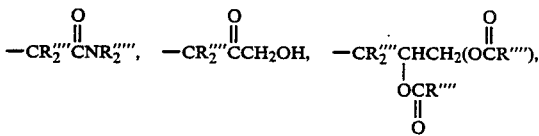

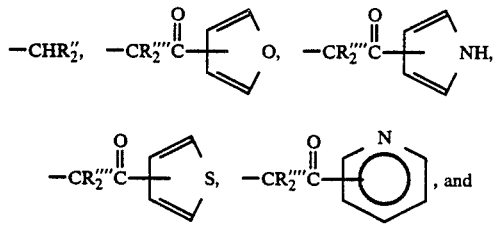

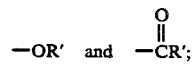

wherein R' is a member of the group consisting of H and lower alkyls ranging from C$_1$ to C$_6$;

wherein R'' is a member of the group consisting of $$-OR' \quad \text{and} \quad -\overset{O}{\underset{\|}{C}}R';$$

wherein R''' is the hydrocarbon backbone of fatty acids;

wherein R'''' is a member of the group consisting of R' and the hydrocarbon backbone of fatty acids;

wherein R''''' is the lower alkyls ranging from C$_1$ to C$_6$; and further, where there are two or more R', R'', R''', R'''', or R''''' groups attached to the same carbon, each R', R'', R''', R'''', or R''''' group may be the same as or different from the other R', R'', R''', R'''', or R''''' groups attached to said carbon.

2. The compound of claim 1, having the formula:

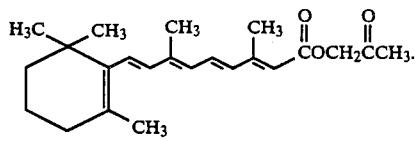

3. A pharmaceutical composition for the treatment of acne which comprises:

an effective acne-treatment amount of an acne-treating compound of the formula:

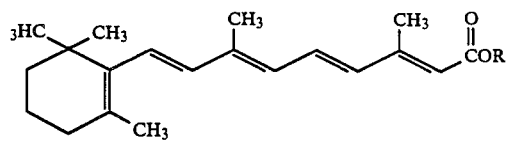

wherein R is a member of the group consisting of:

-continued

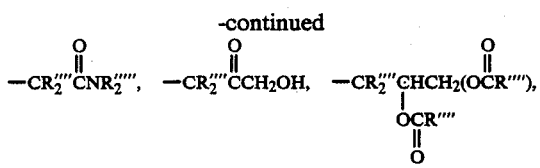

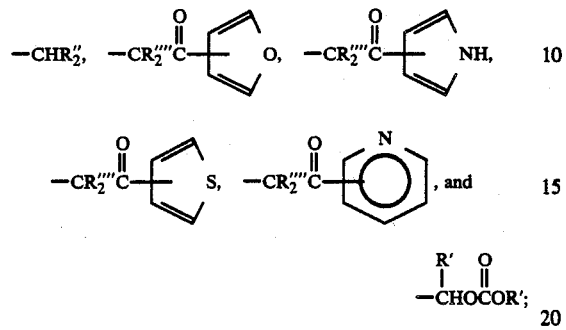

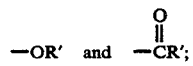

wherein R' is a member of the group consisting of H and lower alkyls ranging from $C_1$ to $C_6$;
wherein R'' is a member of the group consisting of $$-OR' \text{ and } -\overset{O}{\underset{\|}{C}}R';$$

wherein R''' is the hydrocarbon backbone of fatty acids;
wherein R'''' is a member of the group consisting of R' and the hydrocarbon backbone of fatty acids;
wherein R''''' is the lower alkyls ranging from $C_1$ to $C_6$; and further,
where there are two or more R', R'', R''', R'''', or R''''' groups attached to the same carbon, each R', R'', R''', R'''', or R''''' group may be the same as or different from the other R', R'', R''', R'''', or R''''' groups attached to said carbon;
admixed with a pharmaceutically-acceptable vehicle.

4. The composition of claim 3, wherein said acne-treating compound comprises from about 0.01% to about 0.5% by weight of said composition.

5. The composition of claim 3, wherein said acne-treating compound comprises from about 0.05% to about 0.2% by weight of said composition.

6. The composition of claim 3, wherein said vehicle is a mixture selected from the group consisting of propylene glycol-ethanol and propylene glycol-ethanol chloroform.

7. The composition of claim 3, wherein said acne-treating compound has the formula:

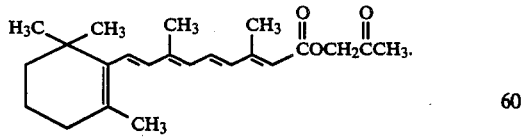

8. A method for treating acne in a subject requiring such treatment which comprises:
topical application to the acne site of said subject of a pharmaceutical composition which comprises an effective acne-treatment amount of a compound of the formula:

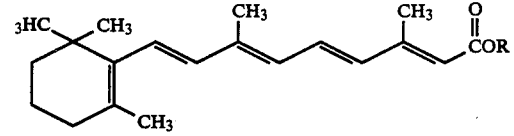

wherein R is a member of the group consisting of:

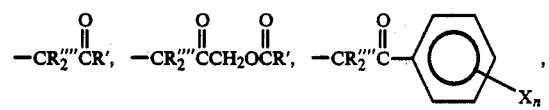

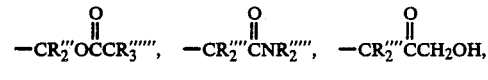

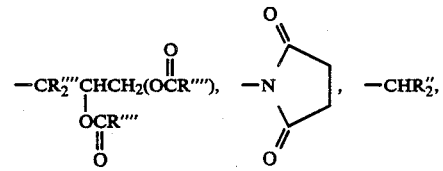

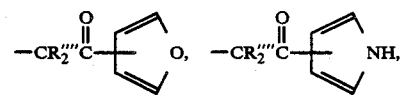

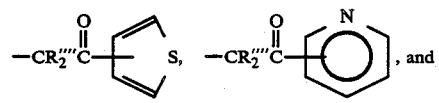

wherein X is a member of the group consisting of:
—H, —F, —Cl, —Br, —I, —OH, —OR, —OR',

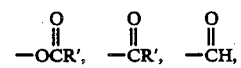

—CN, —NO$_2$, —NH$_2$, —NHR', and —NR'$_2$;
wherein n is a number from 1 to 5;
wherein R' is a member of the group consisting of H and lower alkyls ranging from $C_1$ to $C_6$;
wherein R' is a member of the group consisting of

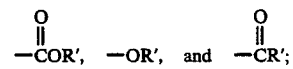

wherein R''' is the hydrocarbon backbone of fatty acids;
wherein R'''' is a member of the group consisting of R' and the hydrocarbon backbone of fatty acids;
wherein R''''' is the lower alkyls ranging from $C_1$ to $C_6$; and further,
where there are two or more R', R'', R''', R'''', or R''''' groups attached to the same carbon, each R', R'', R''', R'''', or R''''' group may be the same as or different from the other R', R'', R''', R'''', or R''''' groups attached to said carbon;

admixed with a pharmaceutically-acceptable topical vehicle.

9. The method of claim 8, wherein said acne-treating compound comprises from about 0.01% to about 0.5% by weight of said composition.

10. The method of claim 8, wherein said acne-treating compound comprises from about 0.05% to about 0.2% by weight of said composition.

11. The method of claim 8, wheren said vehicle is a mixture selected from the group consisting of propylene glycol-ethanol and propylene glycol-ethanol chloroform.

12. The method of claim 8, wherein said acne-treating compound has the formula:

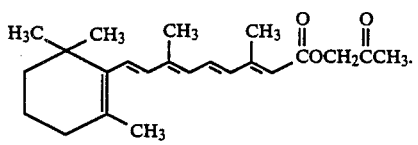

13. The method of claim 8, wherein said acne-treating compound has the formula:

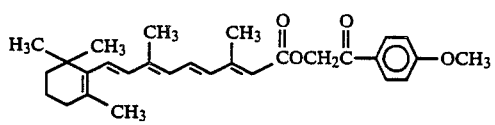

14. A method for treating acne in a subject requiring such treatment which comprises:
oral application to said subject of an effective acne-treatment amount of a compound of the formula:

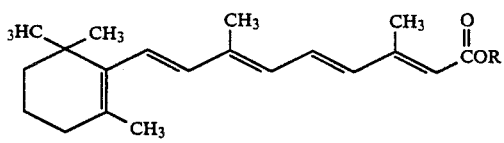

wherein R is a member of the group consisting of:

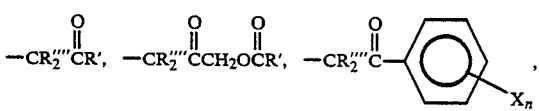

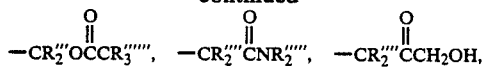

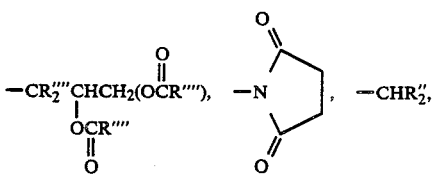

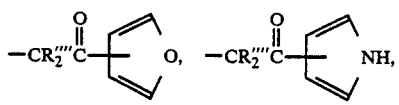

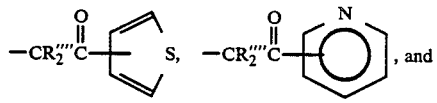

wherein X is a member of the group consisting of:
—H, —F, —Cl, —Br, —I, —OH, —OR, —OR',

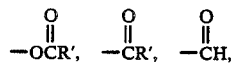

—CN, —NO$_2$, —NH$_2$, —NHR', and —NR'$_2$;
wherein n is a number from 1 to 5;
wherein R' is a member of the group consisting of H and lower alkyls ranging from C$_1$ to C$_6$;
wherein R'' is a member of the group consisting of

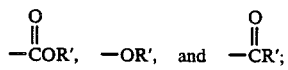

wherein R''' is the hydrocarbon backbone of fatty acids;
wherein R'''' is a member of the group consisting of R' and the hydrocarbon backbone of fatty acids;
wherein R''''' is the lower alkyls ranging from C$_1$ to C$_6$; and further,
where there are two or more R', R'', R''', R'''', or R''''' groups attached to the same carbon, each R', R'', R''', R'''', or R''''' group may be the same as or different from the other R', R'', R''', R'''', or R''''' groups attached to said carbon;
admixed with a pharmaceutically acceptable oral vehicle.

* * * * *